US005605906A

United States Patent [19]

Lau

[11] Patent Number: 5,605,906
[45] Date of Patent: Feb. 25, 1997

[54] CANNABINOID RECEPTOR AGONISTS

[75] Inventor: Cheuk K. Lau, Quebec, Canada

[73] Assignee: Merck Frosst Canada, Inc., Kirkland, Canada

[21] Appl. No.: 410,256

[22] Filed: Mar. 24, 1995

[51] Int. Cl.$^6$ .................... A61K 31/445; C07D 221/12
[52] U.S. Cl. .................................. 514/298; 546/108
[58] Field of Search .................... 546/108; 514/298

[56] References Cited

U.S. PATENT DOCUMENTS

| | | | |
|---|---|---|---|
| 4,228,169 | 10/1980 | Johnson et al. | 424/258 |
| 4,260,764 | 4/1981 | Johnson | 546/153 |
| 4,309,545 | 1/1982 | Johnson | 546/108 |

FOREIGN PATENT DOCUMENTS 854655  5/1977  Belgium .

OTHER PUBLICATIONS

Gogte V N, Salawa, M A, Tilak (1970) Tetrahedron 26, 173–181.
William A. Devane et al., Molecular Pharma, 34, pp. 605–613 (1988).
Sean Munro et al., Nature, 365, pp.61–65 (1993).
Elizabeth A. Frey et al., Eu. J Pharma, 244, pp. 239–250 (1993).
William L. Dewey, Pharma Reviews, 38:2, pp. 151–178 (1986).
John F. Hoops et al., J Org Chem, 33:7, pp. 2995–2996 (1968).
Catherine M. Gerard et al., Biochem J, 279, pp. 129–134, (1991).
W. D. M. Paton, Annual Review Pharma., 15, pp. 191–220 (1975).
H. F. Hardman et al., Proc West Pharma Soc, 14, pp. 14–20 (1971).
William A. Devane et al., J Med Chem, 35:11, pp. 2065–2069 (1992).
Beil, Psychomimeti Drugs, Efron, Raven Press, NY p. 336 (1970).

*Primary Examiner*—C. Warren Ivy
*Assistant Examiner*—Evelyn Huang
*Attorney, Agent, or Firm*—Sylvia A. Ayler; Mark R. Daniel

[57] ABSTRACT

Disclosed are novel cannabinoid (CB2) receptor agonists, their compositions, and the methods of their preparation. The compounds are useful for lowering ocular intra ocular pressure, treating glaucoma, useful as antiinflammatory, immunosuppressive, analgesics agents, and as agents for treatment and prevention of emesis and nausea because of the activity on the cannabinoid receptor.

7 Claims, No Drawings

CANNABINOID RECEPTOR AGONISTS

BACKGROUND OF THE INVENTION

This invention relates to certain novel octahydro-3-alkoxy-9-alkyl-phenanthridines and derivatives thereof and pharmaceutically acceptable acid addition salts thereof useful as antiinflammatory, analgesics, immunosuppressive, antiemetic and intraocular pressure reducing agents for use in mammals, including man; methods for their use and pharmaceutical compositions containing them.

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesics such as d-propoxyphene, codeine, and morphine, possess addictive liability. The need for improved and potent analgesics is, therefore, evident.

The major active ingredient of marijuana, $\Delta^9$-terahydrocannabinol ($\Delta^9$-THC), has been known to exert a wide range of pharmacological effects including analgesia, antiemetic, antiinflammation, immunosuppression, anticonvulsion and reduction of intraocular pressure in glaucoma (Dewley, W. L. Pharmac. Rev. 38, 151–178 (1986)). The clinical application of cannabinoids has, however, beeen limited by their pschoactive effects. In 1988, Devane et al (Mol. Pharmacol. 1988, 34, 605–613) reported the identification of a cannabinoid receptor in the brain (CB 1) which may be involved in cannabinoid-induced alterations in mood and cognition effect experienced by users of Marijuana. Recently a peripheral receptor for cannabinoids (CB2), that is not expressed in the brain but rather in macrophages in the marginal zone of spleen, has been isolated and characterized (Munro et al., Nature, 365, 61–65 (1993)). Thus a selective CB2 agonist can have antiinflammatory, analgesic, antiemetic, immunosuppressive and intraocular pressure reducing properties associated with cannabinoids without the pschoactive effects associated with CB 1 receptors.

It has been shown that certain 1,9-dihydroxy-octahydrobenzo-[c]quinolines (U.S. Pat. Nos. 4,260,764; 4,228,169) as well as the 9-oxo analogs (Belgian Pat. No. 854,655, 1977) are useful as CNS agents especially as analgesics and tranquilizers, as hypotensives, diuretics and as agents for treatment of glaucoma. The corresponding 9-amino and 9-oximino analogs have also been shown to have similar properties (U.S. Pat. No. 4,309,545).

Hoops et al., J. Org. Chem., 33, 2995–2996 (1968) describe the preparation of the 5-aza analog of delta-6a(10a)tetrahydrocannabinol referred to therein as 7,8,9,10-tetrahydro-1-hydroxy-5,6, 6,9-tetramethyl-3-n-pentylphenanthridine, but report no utility for the compound. Beil, in "Psychomimetic Drugs", edited by Efron, Raven Press, New York, 1970, page 336, reports the compound was "completely inert in animal pharmacology."

Hardman et al., Proc. West. Pharmacol. Soc., 14, 14–20 (1971) reports some pharmacological activity for 7,8,9,10-tetrahydro-1-hydroxy -6,6,9-trimethyl-3-n-pentyl phenanthridine, a 5-aza-delta6a(10)a-tetrahydrocannabinol. Paton, in Annual Review of Pharmacology, 15, 192 (1975), presents generalizations on structureaction relationships among cannabinoids. The presence of the gem dimethyl group in the pyran ring is critical for cannabinoid activity and substitution of N for O in the pyran ring removes activity. It has now been found that certain octahydro-3-alkoxy-9-alkyl-phenanthridine and derivatives are selective CB2 receptor agonists and are therfore effective in mammals, including man, as antiinflammatory, immunosuppressive, analgesics agents and useful in the treatment of glaucoma; as agents for treatment and prevention of emesis and nausea, especially that induced by antineoplastic drugs.

SUMMARY OF THE INVENTION

This invention pertains to novel octahydro-3-alkoxy-9-alkyl-phenanthridines and derivatives thereof, which are selective CB2 receptor agonists effective in mammals, including man, as antiinflammatory, immunosuppressive, analgesics agents; as agents in the treatment of glaucoma; and as agents for treatment and prevention of emesis and nausea, especially that induced by antineoplastic drugs. The novel compounds of the instant invention have the formula I:

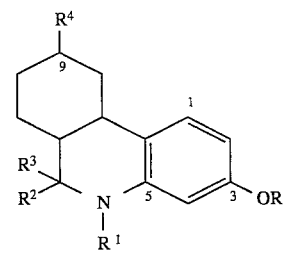

or pharmaceutically acceptable salts thereof, or diastereomers, enantiomers or mixtures thereof, wherein:

R is selected from the group consisting of:
- (1) hydrogen,
- (2) $C_{1-3}$fluoroalkyl,
- (3) $C_{1-6}$alkyl, or
- (4) phenyl or benzyl, optionally substituted with halo, $C_{1-6}$alkyl, $C_{1-6}$alkoxy, $C_{1-6}$alkyltio, CN, $CF_3$, $CO_2H$, or $CO_2C_{1-4}$alkyl;

$R_1$ is selected from the group consisting of:
- (a) hydrogen,
- (b) $C_{1-6}$alkoxy,
- (c) CN,
- (d) $C_{1-3}$fluoroalkyl,
- (e) $C_{1-6}$alkyl,
- (f) —$CO_2$—$C_{1-4}$alkyl,
- (g) —$C(R^5)(R^6)$—O—$C_{1-4}$alkyl, or
- (h) —$C_{1-6}$alkyl—$CO_2$—$R^7$;

$R^2$ and $R^3$ are each independently selected from the group consisting of:
- (a) hydrogen,
- (b) $C_{1-6}$alkoxy,
- (c) $C_{1-6}$alkylthio,
- (d) CN,
- (e) $C_{1-3}$fluoroalkyl,
- (f) $C_{1-6}$alkyl,
- (g) —$CO_2H$,
- (h) —$CO_2$—$C_{1-4}$alkyl,
- (i) —$C(R^5)(R^6)$—OH,
- (j) —$C(R^5)(R^6)$—O—$C_{1-4}$alkyl, or
- (k) —$C_{1-6}$alkyl—$CO_2$—$R^7$;

$R^4$ is selected from the group consisting of:
- (a) hydrogen,
- (b) halo,
- (c) $C_{1-6}$alkoxy,
- (d) $C_{1-6}$alkylthio,
- (e) CN, (f) $C_{1-3}$fluoroalkyl,
(g) $C_{1-6}$alkyl,
(h) $N_3$,
(i) —$CO_2H$,
(j) —$CO_2$—$C_{1-4}$alkyl,
(k) —$C(R^5)(R^6)$—OH,
(l) —$C(R^5)(R^6)$—O—$C_{1-4}$alkyl, or
(m) —$C_{1-6}$alkyl—$CO_2$—$R^7$; and $R^5$, $R^6$ and $R^7$ are each independently selected from the group consisting of:
(a) hydrogen, or
(b) $C_{1-6}$alkyl.

DETAILED DESCRIPTION OF THE INVENTION

The invention encompasses the novel compound of Formula I, a composition thereof, as well as a method of treating inflammation, pain, emesis, and intraocular hypertension comprising administration to a patient in need of such treatment of a non-toxic therapeutically effective amount of a compound of Formula I.

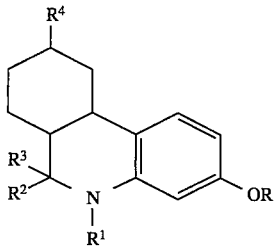

I or pharmaceutically acceptable salts thereof, or diastereomers, enantiomers or mixtures thereof, wherein:
R is selected from the group consisting of:
(1) hydrogen,
(2) $C_{1-3}$fluoroalkyl,
(3) $C_{1-6}$alkyl, or
(4) phenyl or benzyl, optionally substituted with halo, $C_{1-6}$alkyl, $C_{1-6}$alkoxy, $C_{1-6}$alkyltio, CN, $CF_3$, $CO_2H$, or $CO_2C_{1-4}$alkyl;

$R^1$ is selected from the group consisting of:
(a) hydrogen,
(b) $C_{1-6}$alkoxy,
(c) CN,
(d) $C_{1-3}$fluoroalkyl,
(e) $C_{1-6}$alkyl,
(f) —$CO_2$—$C_{1-4}$alkyl,
(g) —$C(R^5)(R^6)$—O—$C_{1-4}$alkyl, or
(h) —$C_{1-6}$alkyl—$CO_2$—$R^7$;

$R^2$ and $R^3$ are each independently selected from the group consisting of:
(a) hydrogen,
(b) $C_{1-6}$alkoxy,
(c) $C_{1-6}$alkylthio,
(d) CN,
(e) $C_{1-3}$fluoroalkyl,
(f) $C_{1-6}$alkyl,
(g) —$CO_2H$,
(h) —$CO_2$—$C_{1-4}$alkyl,
(i) —$C(R^5)(R^6)$—OH,
(j) —$C(R^5)(R^6)$—O—$C_{1-4}$alkyl, or
(k) —$C_{1-6}$alkyl—$CO_2$—$R^7$;

$R^4$ is selected from the group consisting of:
(a) hydrogen,
(b) halo,
(c) $C_{1-6}$alkoxy,
(d) $C_{1-6}$alkylthio,
(e) CN,
(f) $C_{1-3}$fluoroalkyl,
(g) $C_{1-6}$alkyl,
(h) $N_3$,
(i) —$CO_2H$,
(j) —$CO_2$—$C_{1-4}$alkyl,
(k) —$C(R^5)(R^6)$—OH,
(l) —$C(R^5)(R^6)$—O—$C_{1-4}$alkyl, or
(m) —$C_{1-6}$alkyl—$CO_2$—$R^7$; and $R^5$, $R^6$ and $R^7$ are each independently selected from the group consisting of:
(a) hydrogen, or
(b) $C_{1-6}$alkyl.

A preferred embodiment of the novel compounds of this invention is wherein:
R is selected from the group consisting of:
(1) hydrogen,
(2) $C_{1-6}$alkyl, or
(3) phenyl or benzyl, optionally substituted with halo, $C_{1-6}$alkyl, $C_{1-6}$alkoxy, $C_{1-6}$alkyltio, CN, $CF_3$, $CO_2H$, or $CO_2C_{1-4}$alkyl;

$R^1$ is selected from the group consisting of:
(a) hydrogen,
(b) $C_{1-6}$alkoxy,
(c) CN,
(d) $C_{1-3}$fluoroalkyl, or
(e) $C_{1-6}$alkyl, $R^2$ and $R^3$ are each independently selected from the group consisting of:
(a) hydrogen,
(b) $C_{1-6}$alkoxy,
(c) $C_{1-6}$alkylthio,
(d) CN,
(e) $C_{1-3}$fluoroalkyl,
(f) $C_{1-6}$alkyl,
(g) —$CO_2H$, or
(h) —$CO_2$—$C_{1-4}$alkyl;

$R^4$ is selected from the group consisting of:
(a) hydrogen,
(b) halo,
(c) $C_{1-6}$alkoxy,
(d) $C_{1-6}$alkylthio,
(e) CN,
(f) $C_{1-3}$fluoroalkyl,
(g) $C_{1-6}$alkyl,
(h) $N_3$; and $R^5$, $R^6$ and $R^7$ are each independently selected from the group consisting of:
(a) hydrogen, or
(b) $C_{1-6}$alkyl.

A most preferred embodiment of the novel compounds of this invention is wherein: R, $R^1$, $R^2$, $R^3$ and $R^4$ is $C_{1-6}$alkyl.

For purposes of this specification, alkyl is defined to include linear, branched, and cyclic structures, with $C_{1-6}$alkyl including, but not restricted to, methyl, ethyl, propyl, 2-propyl, n-, i-, s- and t-butyl, pentyl, hexyl, 1,1- dimethylethyl, cyclopropyl, cyclobutyl, cyclopentyl or cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, n-propylthio, isopropylthio, cyclohexylthio, etc. By way of illustration, the propylthio group signifies —$SCH_2CH_2CH_3$. $C_{1-6}$fluoroalkyl includes alkyl groups of from 1 to 6 carbon atoms of a straight, branched or cyclic configuration, in which one or more hydrogen is replaced by fluorine. Examples are —$CH_2F$, $CHF_2$, —$CF_3$, —$CH_2CF_3$, c-pr-$F_5$, c-Hex-$F_{11}$, and the like. Halo includes F, Cl, Br, or I.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Exemplifying the invention are;
(a) 3-Methoxy-5,6,6,9-tetramethyl5,6,6a,7,8,9,10,10a-octahydro-phenanthridine
(b) 3-Hexyloxy-5,6,6,9-tetramethyl5,6,6a,7,8,9,10,10a-octahydro-phenanthridine
(c) 3-Methoxy-5,6,6-trimethyl9-hydroxymethyl-5,6,6a,7,8,9,10,10a-octahydro-phenanthridine
(d) 3-Methoxy-5,6-dimethyl6-propyl9-hydroxymethyl-5,6,6a,7,8,9,10,10a-octahydro-phenanthridine This invention is also concerned with pharmaceutical compositions for activating cannabinoid ($CB_2$) receptors and for treating cannabinoid ($CB_2$) receptor mediated diseases as disclosed herein, comprising a pharmaceutically acceptable carrier and a nontoxic therapeutically effective amount of compound of Formula I as described above.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The ability of the compounds of formula I to mimic the actions of the cannabinoids makes them useful for preventing or reversing the symptoms that can be treated with cannabis, some of its derivatives and synthetic cannabinoids in a human subject. Thus, compounds of formula I are useful to treat, prevent, or ameliorate in mammals and especially in humans:

1 - various ocular disorders such as glaucoma, ocular hypertension.
2 - pulmonary disorders including diseases such as asthma, chronic bronchitis and related airway diseases.
3 - allergies and allergic reactions such as allergic rhinitis, contact dermatitis, allergic conjunctivitis and the like.
4 - inflammation such as arthritis or inflammatory bowel disease.
5 - pain.
6 - disorders of the immune system such as lupus, AIDS, etc.
7 - allograft rejection.
8 - vomiting, and nausea and vertigo, especially in the case of chemotherapy patients Dose Ranges The magnitude of therapeutic dose of a compound of Formula I will, of course, vary with the nature of the severity of the condition to be treated and with the particular compound of Formula I and its route of administration and vary upon the clinician's judgment. It will also vary according to the age, weight and response of the individual patient. An effective dosage amount of the active component can thus be determined by the clinician after a consideration of all the criteria and using is best judgment on the patient's behalf.

An ophthalmic preparation for ocular administration comprising 0.001–1% by weight solutions or suspensions of the compounds of Formula I in an acceptable ophthalmic formulation may be used.

Pharmaceutical Compositions

Any suitable route of administration may be employed for providing a mammal, especially a human with an effective dosage of a compound of the present invention. For example, oral, parenteral and topical may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, parenteral and ocular (ophthalmic). They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carders such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carder which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combinations with Other Drugs

In addition to the compounds of Formula I, the pharmaceutical compositions of the present invention can also contain other active ingredients or prodrugs thereof. These other active species may be β-blockers such as timolol, topical carbonic anhydrase inhibitors such as Dorzolamide, systemic carbonic anhydrase inhibitors such as acetolamide, cholinergic agents such as pilocarpine and its derivatives, prostaglandin F receptor agonists such as Latanoprost, ajmaline and its derivatives, $\beta_2$ adrenergic agonists such as epinephrine, glutamate antagonists, aminosteroids, diuretics, and any other compound used alone or in combination in the treatment of glaucoma. The weight ratio of the compound of the Formula I to the second active ingredient may be varied and will depend upon the effective dose of each ingredient. Generally, an effective dose of each will be used. Thus, for example, when a compound of the Formula I is combined with a β-blockers, a carbonic anhydrase inhibitor, a pilocarpine derivative or a prostaglandin agonist, the weight ratio of the compound of the Formula I to the other drug will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis

Compounds of the present invention can be prepared according to the following non-limiting method, which is depicted in Scheme 1 below. Temperatures are in degrees Celsius.

Reaction of a 3-alkoxy-N-($R^1$)aniline with phenyl dichloroborane in refluxing dichloroethane gives a N-($R^1$)-3-alkoxyanilinochlorophenylborane. Reaction of the latter with various substituted heptenals gives 1-(4-alkoxy-2-($R^1$)amino-phenyl)-hept-6-en-1-ol which cyclizes to I when heated in the presence of phenyl boronic acid.

SCHEME 1

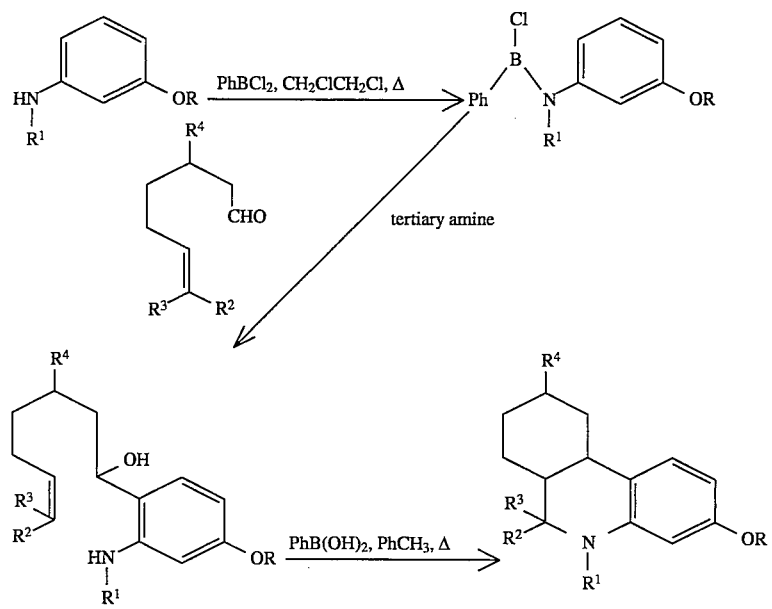

I where: R, $R^1$, $R^2$, $R^3$ and $R^4$ are described above. Table 1 below illustrates compounds of Formula I, which are representative of the present invention.

TABLE 1

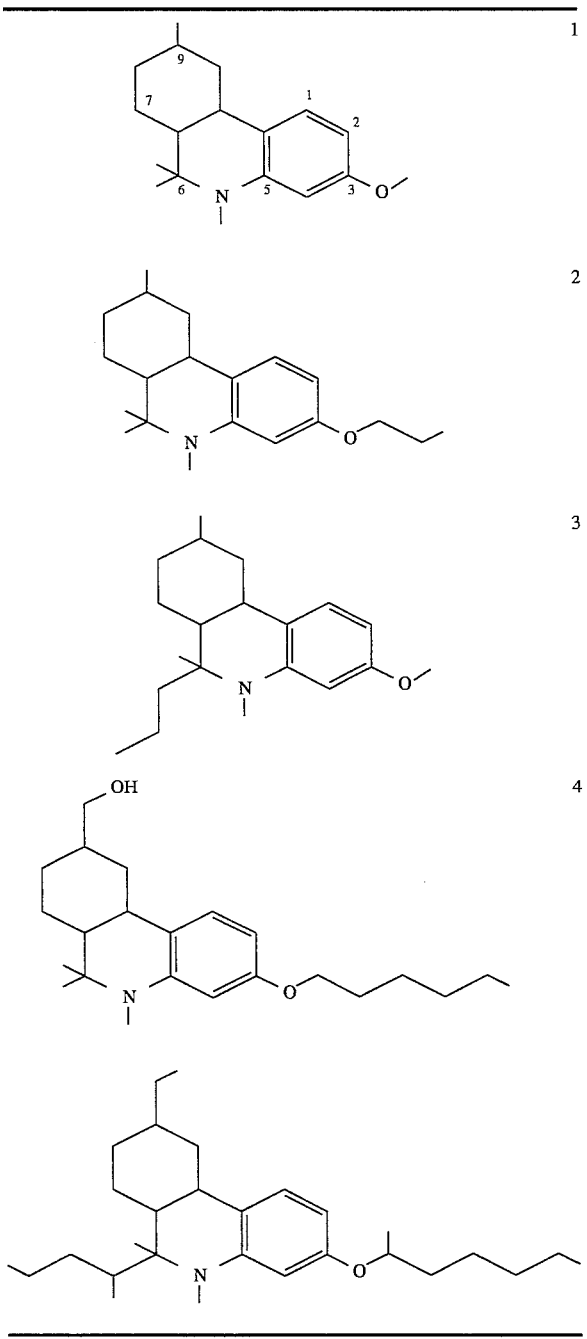

1. 3-methoxy-5,6,6,9-tetramethyl-5,6,6a,7,8,9,10,10a-octahydrophenanthridine
2. 3-propyloxy-5,6,6,9-tetramethyl5,6,6a,7,8,9,10,10a-octahydrophenanthridine
3. 3-methoxy-5,6,9-trimethyl6-propyl5,6,6a,7,8,9,10,10a-octahydrophenanthridine
4. 3-hexyloxy-5,6,6-trimethyl9-hyroxymethyl-5,6,6a,7,8,9,10,10a-octahydrophenanthridine
5. 3-(2-heptyloxy)-5,6-dimethyl6-(2-pentyl)-9-ethyl-5,6,6a,7,8,9,10,10a-octahydrophenanthridine Assays for determining Biological Activity The compound of Formula I can be tested using the following assays to determine their affinity for binding to the cannabinoid receptors.

CB2 and CB1 Receptor Membrane Preparation

Stable cell lines were constructed expressing either the human peripheral cannabinoid (CB2) receptor or the human central cannabinoid (CB 1) receptor as described previously (Gerard. et al., Molecular cloning of a human cannabinoid receptor which is also expressed in testis. Biochem. J. (279)129–134, 1991.). Membranes were prepared from CHO-K1 cells stably expressing the CB2 receptor and HEK293(EBNA) cells stably expressing the CB 1 receptor by differential centrifugation (1000×g for 10 min, then 100,000×g for 30 min, both at 4° C.) following lysis of the cells by nitrogen cavitation at 800 psi for 15 min on ice, as previously described (Frey, E.A., et al., Characterization of the leukotriene $D_4$ receptor in dimethylsulphoxide-dufferentiated U937 cells: comparison with the leukotriene $D_4$ receptor in human-lung and guinea-pig lung. Eur. J. Pharma. (244) 239–250, 1993.). The 100,000×g membrane fraction was resuspended at a protein concentration of 3–5 mg/ml by Dounce homogenization (Pestle A; 10 strokes), frozen in liquid nitrogen and stored in aliquots at –80° C.

CB2 and CB1 Receptor Binding Assays

CB2 receptor binding assays were performed in 0.2 ml of 10 mM HEPES/KOH (pH 7.4) containing 1 mM EDTA, 0.3 mg/ml human serum albumin (HSA), 1 mM $MgCl_2$, and 2.4 nM [$^3$H]Win 55212-2 (Dupont-NEN Canada, Mississauga, ON). CB1 receptor binding assays were performed in 0.2 ml of 10 mM HEPES/KOH (pH 7.4) containing 1 mM EDTA, 0.3 mg/ml human serum albumin (HSA), 3 mM $MgCl_2$, and 0.6 nM [$^3$H]CP55940(–)(Dupont-NEN Canada, Mississauga, ON). The reactions were initiated with the addition of either12–15 mg CB2 - CHO—K1 protein or 6–9 mg $CB_1$-HEK293(EBNA) protein from the 100,000×g membrane fraction. Samples were incubated for either 40 or 60 rain (CB2 or CB 1 receptor binding assay respectively) at 30° C. prior to separation of the bound and free radioligand by rapid filtration using GF/B or GF/C filters (CB2 or CB 1 receptor binding assays respectively) as previously described (Frey et al., 1993). The residual [$^3$H]Win 55212-2 or [$^3$H]CP55940(–) bound to the filters was determined by liquid scintillation counting following a 6h equilibration in 5 ml BiofluorÔ) (Dupont-NEN Canada, Mississauga, ON) scintillation cocktail (efficiency for tritium was approximately 55%). Specific binding was defined as the difference between total binding and non-specific binding which was determined in samples containing 1 mM Win 55212-2 or 1 mM HU-210 (CB2or CB1 receptor binding assays respectively). Under these binding assay conditions, total binding represented approximately 10 –15% of the radioligand added to the incubation mixture, with specific binding representing 85–90% or 55–60% (CB2 or CB 1 receptor binding assays respectively) of the total binding. In addition, total binding was in the linear range with respect to the protein and radioligand concentrations used in the assay.

cAMP Assays in CHO-K1 Cells Expressing the CB2 Receptor

CB2—CHO-K1 cells were seeded at $10^6$ cells per 175 $cm^2$ T-flask in MEM alpha growth medium (MEM alpha medium containing 25 mM HEPES/KOH (pH 7.4), 10% heat inactivated fetal bovine serum, 20 units/ml penicillin G, 20 mg/ml streptomycin sulfate and 500 mg/ml G418) (GIBCO-BRL Canada, Burlington, ON). The cells were maintained in culture for three days and the medium was replaced 16–24 h prior to harvesting the cells. Cells were harvested at approximately 80% confluence by incubation in enzyme-free cell dissociation buffer, washed once with HEPES-buffered Krebs—Ringer solution {1.25 mM $MgSO_4$, 1.5 mM $CaCl_2$, 5 mM KCl, 124 mM NaCl, 8 mM glucose, 1.25 mM $KH_2PO_4$, and 25 mM HEPES/KOH (pH 7.4)} containing 1 mg/ml HSA and resuspended in the same buffer. The cAMP assay was performed in a final volume of 0.2 ml of HEPES-buffer Krebs-Ringer solution containing 1 mg/ml HSA, 100 mM of the phosphodiesterase type IV inhibitor RO-20-1724 and 5 mM forskolin (Biomol, Plymouth Meeting, Pa.). RO-20-1724, forskolin and the compounds under evaluation were added to the incubation mixture in dimethyl sulfoxide ($Me_2SO$) or ethanol to a final vehicle concentration 0.35% (v/v) which was kept constant in all samples. The reaction was initiated by the addition of $10^5$ cells per incubation. Samples were incubated at 37° C. for 15 min and the reaction was then terminated by immersing the samples in boiling water for 3 min. Cell viability was always >96% as determined by trypan blue exclusion. Measurement of cAMP was performed by radioimmunoassay using [$^{125}$I]cAMP (Amersham Canada, Oakville, ON).

Biological Data

Compounds of the present invention are agonists of the cannabinoid (CB2) receptor and are thereby useful in the treatment of diseases that can be treated by cannabinoids. The affinities of the compounds for the cannabinoid receptors CB1 and CB2 may be seen in the representative results shown below. For comparison purposes, the Table also contains data for a known potent cannabinoid mimic (HU210) (Devane, W. A., Breuer, A., Sheskin, T., Jarbe, T. U. C., Eisen, M. S. and Mechoulam, R., A Novel Probe for the Cannabinoid Receptor. J. Am. Chem. Soc. (35), 2065, 1992.) which is a non-selective cannabinoid receptor agonist.

|  | CB2 binding assay $K_i$ (nM) | CB1 binding assay $IC_{50}$ (nM) | CB2 functional assay $EC_{50}$ (nM) |
| --- | --- | --- | --- |
| Example 1 | 73, 55 | 22300, 27400 | 68, 149 |
| HU-210 | 0.36 ± .05 | 2.5 ± 0.2 | 0.37 ± 0.07 |

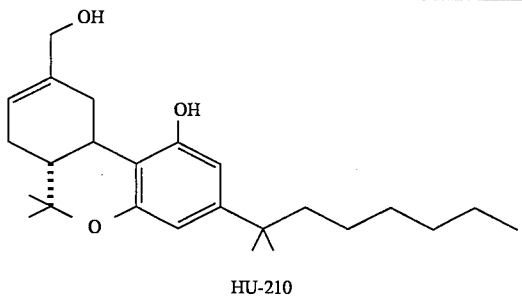

HU-210

Alkyl group abbreviations

Me = methyl
Et = ethyl
n-Pr = normal propyl
i-Pr = isopropyl
n-Bu = normal butyl
i-Bu = isobutyl
s-Bu = secondary butyl
t-Bu = tertiary butyl
c-Pr = cyclopropyl
c-Bu = cyclobutyl
c-Pen = cyclopentyl
c-Hex = cyclohexyl The invention will now be illustrated by the following non-limiting examples in which, unless stated otherwise:

(i) all operations were carried out at room or ambient temperature, that is, at a temperature in the range 18°–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and "d" indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in pans per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

(6aR,9R,10aR)-3-Methoxy-5,6,6,9-tetramethyl-5,6,6a,7,8,9,10,10a-octahydro-phenanthridine Step 1: N-methyl-3-methoxyanilinochlorophenylborane N-methyl-3-methoxyanilinochlorophenylborane was prepared by adding dichlorophenylborane (100 mmol) to a solution of N-methy-3-methoxyaniline (100 mmol) in 1,2-dichloroethane (100 mL) at 0° C. The resulting mixture was refluxed for 2 h under a rapid stream of nitrogen to remove the HCl formed. The mixture was cooled to give a 0.8 M cloudy solution of the title compound which could be stored at 0°C. for more than 6 weeks without deterioration.

Step 2: (3R)-1-(2-Methoxy-6-methylamino-phenyl)-3,7-dimethyl-oct-6-en-1-ol and (3R)-1-(2-Methylamino-4-methoxy-phenyl)-3,7-dimethyl-oct-6-en-1-ol A solution of N-methyl-3-methoxyanilinochlorophenylborane (11 mmol) in dichloroethane was added dropwise to a mixture of (R)-(+)-citronellal (1.54 g, 10 mmol) and diisopropylethylamine (20 mmol) in dichloromethane at −20° C. The mixture was stirred at −20° C. for 2 h and at 20° C. for 0.5 hours, quenched with ammonium acetate and then faltered through a short pad of silica gel. The filtrate was concentrated and the residue was chromatographed on silica gel and eluted with EtOAc/Hexane (0–20%) to afford 32% of (3R)-1-(2-methoxy-6-methylamino-phenyl)-3,7-dimethyl-oct-6-en- 1-ol and 34% of (3R)-1-(2-methylamino-4-methoxy-phenyl)-3,7-dimethyl-oct-6-en- 1-ol. The former is an inseparable 1:1 mixture of diastereomers: $^1$H nmr (400 MHz, $CD_3COCD_3$), resolved signals: δ 0.91 (d, 3H, J=6.6 Hz), 0.95 (d, 3H, J=6.6 Hz), 1.56 (s, 3H), 1.60 (s, 3H), 1.63 (s, 3H), 1.66 (s, 3H), 2.76 (s, 3H, N—$CH_3$), 2.77 (s, 3H, N—$CH_3$), 3.72 (s, 3H, $OCH_3$), 3.73 (s, 3H, $OCH_3$), 4.32 (d, 1H, J=3.5 Hz, OH), 4.34 (d, 1H, J=3.6 Hz, OH), 5.05 (bt, 1H, J =7.1 Hz, CH═C), 5.12 (bt, 1H, J =7.1 Hz, CH═C), 5.50 (m, 2H, CHO), 6.05 (bs, 2H, NH), 6.23 (d, 2H, J=8.3 Hz), 6.25 (d, 4H, J=8.2 Hz), 7.00 (t, 1H, J=8.2 Hz); other resonances: δ 1.15 (m, 2H), 1.30 (m, 2H), 1.40 (m, 2H), 1.50 (m, 2H), 1.70 (m, 2H), 2.0 (m, 4H). Exact Mass calcd. for $C_{18}H_{30}NO_2$ (M+1): 292.2276; found: 292.2276. The two diastereomers of (3R)-1-(2omethylamino-4-methoxy-phenyl)-3,7-dimethyl-oct-6-en-1-ol were separated by repeated chromatography. The less polar isomer: $^1$H nmr (400 MHz, $CD_3COCD_3$), δ 5 0.91 (d, 3H, J=6.6 Hz), 1.18 (m, 1H), 1.42 (m, 2H), 1.60 (s, 3H), 1.66 (s, 3H), 1.65 (m, 2H), 1.97 (m, 2H), 2.78 (d, 3H, J=5.2 Hz, N—$CH_3$), 3.73 (s, 3H), 4.13 (d, 1H, J=4 Hz, OH), 4.72 (m, 1H, CHO), 5.12 (bt, 1H, J=7.2 Hz, CH═C), 5.48 (bs, 1H, NH), 6.11 (d, 1H, J=8.3 Hz), 6.88 (d, 1H, J=8.8 Hz); $^{13}$C nmr (100.6 MHz, $CD_3COCD_3$),: 17.7, 19.6, 25.9, 26.2, 30.4, 38.5, 55.1, 72.1, 97.7, 100.3, 122.5, 125.8, 131.3, 150.2, 161.1; the more polar isomer: $^1$H nmr (400 MHz, $CD_3COCD_3$), δ 0.94 (d, 3H, J=6.8 Hz), 1.13 (m, 1H), 1.40 (m, 1H), 1.48 (m, 1H), 1.56 (s, 3H), 1.63 (s, 3H), 1.65 (m, 2H), 1.80 (m, 1H), 1.95 (m, 1H), 2.78 (d, 3H, J=5.2 Hz, N—$CH_3$), 3.73 (s,3H), 4.16 (d, 1H, J=3.9 Hz, OH), 4.70 (m, 1H, CHO), 5.05 (bt, 1H, J=7.2 Hz, CH═C), 5.48 (bs, 1H, NH), 6.10 (d, 1H, J=7.4 Hz), 6.12 (s, 1H), 6.86 (d, 1H, J=7.8 Hz); $^{13}$C nmr (100.6 MHz, $CD_3COCD_3$), δ 5 17.8, 20.6, 25.9, 26.1, 30.2, 30.4, 37.7, 43.3, 55.1, 72.9, 97.7, 100.3, 121.9, 125.8, 128.7, 131.2, 150.3, 161.2; Exact Mass calcd. for $C_{18}H_{30}NO_2$ (M+1): 292.2276; found: 292.2276.

Step 3: (6aR,9R,10aR)-3-Methoxy-5,6,6,9-tetramethyl-5,6,6a,7,8,9,10,10a-octahydro-phenanthridine A mixture of (3R)-1-(2-methylamino-4-methoxy-phenyl)3,7-dimethyl-oct-6-en-1-ol (291 mg, 1 mmol), phenylboronic acid (365 mg, 3 mmol) and propionic acid (22 rag, 0.3 mmol) in benzene (10 mL) was refluxed for 20 h to give, after chromatography, 140 mg (51%) of (6aR,9 R, 10aR)-3-methoxy-5,6,6,9-tetramethyl-5,6,6a,7,8,9,10,10a-octahydro-phenanthridine: $[\alpha]_D$+37 (c 4.5, $CHCl_3$); $^1$H nmr (400 MHz, $CD_3COCD_3$), δ 0.83 (q, 1H, J=11.6 Hz, H-10ax), 0.98 (d, 3H, J=6.5 Hz), 1.0 (s, 3H), 1.20 (m, 2H), 1.22 (m, 1H), 1.29 (s, 3H), 1.54 (m, 1H), 1.82 (m, 1H), 1.89 (m, 1H), 2.37 (dr, 1H, J=10.3, 2.7 Hz), 2.45 (m, 1H), 2.83 (s, 3H), 3.71 (s, 3H), 6.12 (d, 1H, J=2.4 Hz), 6.16 (dd, 1H, J=8.3, 2.4 Hz), 7.0 (d, 1H, J=8.3 Hz); $^{13}$C nmr (100.6 MHz, $CD_3COCD_3$), δ 19.1, 23.1, 26.5, 28.7, 32.4, 33.0, 35.8, 36.0, 41.3, 48.9, 55.1, 57.7, 99.2, 100.7, 120.2, 125.9, 147.8, 160.0. Exact Mass calcd. for $C_{18}H_{28}NO$ (M+1): 274.2170; found: 274.2172.

What is claimed is:

1. A compound of structural formula I:

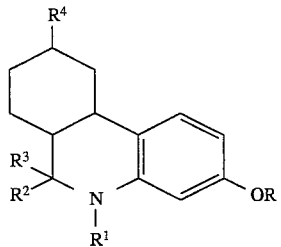

I or pharmaceutically acceptable salts thereof, or diastereomers, enantiomers or mixtures thereof, wherein:

R is selected from the group consisting of:
- (1) hydrogen,
- (2) $C_{1-3}$fluoroalkyl,
- (3) $C_{1-6}$alkyl, or
- (4) phenyl or benzyl, optionally substituted with halo, $C_{1-6}$alkyl, $C_{1-6}$alkoxy, $C_{1-6}$alkyltio, CN, $CF_3$, $CO_2H$, or $CO_2C_{1-4}$alkyl;

$R^1$ is selected from the group consisting of:
- (a) hydrogen,
- (b) $C_{1-6}$alkoxy,
- (c) CN,
- (d) $C_{1-3}$fluoroalkyl,
- (e) $C_{1-6}$alkyl,
- (f) —$CO_2$—$C_{1-4}$alkyl,
- (g) —$C(R^5)(R^6)$—$C_{1-4}$alkyl, or
- (h) —$C_{1-6}$alkyl—$CO_2$—$R^7$;

$R^2$ and $R^3$ are each independently selected from the group consisting of:
- (a) hydrogen,
- (b) $C_{1-6}$alkoxy,
- (c) $C_{1-6}$alkylthio,
- (d) CN,
- (e) $C_{1-3}$fluoroalkyl,
- (f) $C_{1-6}$alkyl,
- (g) —$CO_2H$,
- (h) —$CO_2$—$C_{1-4}$alkyl,
- (i) —$C(R^5)(R^6)$—OH,
- (j) —$C(R^5)(R^6)$—O—$C_{1-4}$alkyl, or
- (k) —$C_{1-6}$alkyl—$CO_2$—$R^7$;

$R^4$ is selected from the group consisting of:
- (a) halo,
- (b) $C_{1-6}$alkoxy,
- (c) $C_{1-6}$alkylthio,
- (d) CN,
- (e) $C_{1-3}$fluoroalkyl,
- (f) $C_{1-6}$alkyl,
- (g) $N_3$,
- (h) —$CO_2H$,
- (i) —$CO_2$—$C_{1-4}$alkyl,
- (j) —$C(R^5)(R^6)$—OH,
- (k) —$C(R^5)(R^6)$—O—$C_{1-4}$alkyl, or
- (l) —$C_{1-6}$alkyl—$CO_2$—$R^7$; and $R^5$, $R^6$ and $R^7$ are each independently selected from the group consisting of:
- (a) hydrogen, or
- (b) $C_{1-6}$alkyl.

2. The compounds of claim 1, wherein,

R is selected from the group consisting of:
- (1) hydrogen,
- (2) $C_{1-6}$alkyl, or
- (3) phenyl or benzyl, optionally substituted with halo, $C_{1-6}$alkyl, $C_{1-6}$alkoxy, $C_{1-6}$alkyltio, CN, $CF_3$, $CO_2H$, or $CO_2C_{1-4}$alkyl;

$R^1$ is selected from the group consisting of:
- (a) hydrogen,
- (b) $C_{1-6}$alkoxy,
- (c) CN,
- (d) $C_{1-3}$fluoroalkyl, or
- (e) $C_{1-6}$alkyl, $R^2$ and $R^3$ are each independently selected from the group consisting of:
- (a) hydrogen,
- (b) $C_{1-6}$alkoxy,
- (c) $C_{1-6}$alkylthio,
- (d) CN, (e) $C_{1-3}$fluoroalkyl,
(f) $C_{1-6}$alkyl,
(g) —$CO_2H$, or
(h) —$CO_2$—$C_{1-4}$alkyl;

$R^4$ is selected from the group consisting of:
(a) halo,
(b) $C_{1-6}$alkoxy,
(c) $C_{1-6}$alkylthio,
(d) CN,
(e) $C_{1-3}$fluoroalkyl,
(f) $C_{1-6}$alkyl,
(g) $N_3$; and $R^5$, $R^6$ and $R^7$ are each independently selected from the group consisting of:
(a) hydrogen, or
(b) $C_{1-6}$alkyl.

3. The compounds of claim 2, wherein: R, $R^1$, $R^2$, $R^3$ and $R^4$, independently is $C_{1-6}$alkyl.

4. The compound of claim 1 which is:
3-Methoxy-5,6,6,9-tetramethyl-5,6,6a,7,8,9,10,10a-octahydrophenanthridine,
3-Hexyloxy-5,6,6,9-tetramethyl-5,6,6a,7,8,9,10,10a-octahydrophenanthridine,
3-Methoxy-5,6,6-trimethyl-9-hydroxymethyl-5,6,6a,7,8,9,10,10a-octahydro-phenanthridine, or
3-Methoxy-5,6-dimethyl-6-propyl-9-hydroxymethyl-5,6,6a,7,8,9,10,10a-octahydro-phenanthridine.

5. A method of treating ocular hypertension and glaucoma, which comprises the step of ocularly administering a pharmacologically effective amount of a cannabimimetic compound of claim 1, to a patient in need of such treatment by selective binding to CB2 receptor.

6. A method of treating ocular hypertension and glaucoma, which comprises the step of ocularly administering a pharmacologically effective amount of a compound of claim 1, to a patient in need of such treatment.

7. A composition useful for treating ocular hypertension and glaucoma in a mammal, including humans, in need thereof, which comprises a pharmacologically effective amount of a cannabimimetic pharmacological agent of claim 1, known to be selective for CB2 receptors, in a carrier or diluent buffered to a pH suitable for ocular administration.

* * * * *